United States Patent [19]

Lawter et al.

[11] Patent Number: 5,114,946

[45] Date of Patent: * May 19, 1992

[54] TRANSDERMAL DELIVERY OF PHARMACEUTICALS

[75] Inventors: James R. Lawter, Orange, N.Y.; John M. Pawelchak, Park Ridge, N.J.

[73] Assignee: American Cyanamid Company, Stamford, Conn.

[*] Notice: The portion of the term of this patent subsequent to Feb. 12, 2008 has been disclaimed.

[21] Appl. No.: 645,942

[22] Filed: Jan. 25, 1991

Related U.S. Application Data

[63] Continuation of Ser. No. 283,204, Dec. 12, 1988, Pat. No. 4,992,445, which is a continuation-in-part of Ser. No. 61,842, Jun. 12, 1987, abandoned.

[51] Int. Cl.⁵ .............................................. A61K 31/44
[52] U.S. Cl. ..................................................... 514/279
[58] Field of Search ........................................ 514/279

[56] References Cited

U.S. PATENT DOCUMENTS

| 4,284,634 | 8/1981 | Sato | 424/266 |
| 4,338,322 | 7/1982 | Sato | 424/266 |

FOREIGN PATENT DOCUMENTS

| 131288 | 4/1980 | European Pat. Off. |
| 164588 | 5/1985 | European Pat. Off. |
| 2940833 | 4/1980 | Fed. Rep. of Germany |

OTHER PUBLICATIONS

Patent Abstract of Japan, vol. 10, No. 131 (C-346) (2188), and JP-A-60 258179 (Yamamouchi).

J. Cardiovasc. Pharmacol., vol. 8, No. 2, pp. 221-226 (1986).

*Primary Examiner*—S. J. Friedman
*Attorney, Agent, or Firm*—Thomas S. Szatkowski

[57] ABSTRACT

Compositions and methods for the transdermal delivery of pharmacologically active chiral compounds are described which are based on the use of enantiomers or mixtures that contain a disproportionate amount of the enantiomers.

6 Claims, No Drawings

TRANSDERMAL DELIVERY OF PHARMACEUTICALS

This is a continuation of copending application Ser. No. 07/283,204 filed Dec. 12, 1988 now U.S. Pat. No. 4,992,445, which is a continuation-in-part of Ser. No. 061,842, filed Jun. 12, 1987, now abandoned.

FIELD OF THE INVENTION

This invention is concerned with the transdermal administration of enantiomers or mixtures of enantiomers of pharmacologically active chiral compounds.

BACKGROUND OF THE INVENTION

A transdermal delivery system is a pharmaceutical composition of matter which is applied to the skin in order to deliver a drug through the skin so as to achieve a systemic therapeutic effect as distinguished from a local therapeutic effect.

If a drug exhibits transdermal fluxes that are too low to provide the desired effect, a flux enhancer may be utilized to increase the transdermal flux. A flux enhancer is a substance, usually a solvent or vehicle, that is applied to the skin in combination with a drug to increase the transdermal flux of the drug. Enhancers are believed to function by disrupting the skin barrier or by changing the partitioning behavior of the drug to the skin.

With or without an enhancer, the transdermal flux determines whether percutaneous administration will provide sufficient drug absorption to achieve therapeutic systemic concentrations. Transdermal flux is a function of the drug's molecular diffusivity, partition coefficient and solubility in the skin.

The applicants have discovered that certain pharmacologically active chiral compounds may be administered transdermally as the resolved pure enantiomer or as a enantiomeric mixture containing a disproportionate amount of one enantiomer and substantially higher fluxes will be achieved than with the transdermal administration of a racemic modification of the same compound using the same vehicle system. It will be understood when reference is made to the enantiomer it is meant also include the substantially pure enantiomer which may contain very small amounts of the other enantiomer.

Accordingly, it is a primary object of this invention to provide compositions of an enantiomer of a pharmacologically active chiral compound or an enantiomeric mixture containing a disproportionate mixture of one enantiomer of a pharmacologically active chiral compound with or without a flux enhancer that will provide high transdermal flux when applied to the skin.

It is also an object of the invention to provide a novel method of transdermally administering pharmacologically active compositions which contain an enantiomer or an enantiomeric mixture containing a disproportionate amount of a pharmacologically active chiral compound.

As used herein and in the appended claims, the term enantiomeric mixture is used to define a mixture containing two enantiomers in any proportion. The term racemic modification is used to define an assembly of chiral molecules one-half of which are mirror images of the other. In the solid state, enantiomeric mixtures may be classified as (1) racemic conglomerates, (2) racemic compounds or (3) solid solutions. This classification appears in H.W.B. Roozeboom, Z. Physik. Chem. 28, 494 (1899); H. Mariser, Chem. Ber. 90,307 (1957) and Eliel, E.L., Stereochemistry of Carbon Compounds, McGraw Hill Book Co., Inc. NY 1962, Chapter 4, pp. 31-86 which are incorporated by reference. The term disproportionate mixture of enantiomers is used to include enantiomeric mixtures having other than 50:50 ratio of enantiomers.

SUMMARY OF THE INVENTION

The invention provides novel compositions containing a (+) or (−) enantiomer of a pharmacologically active chiral compound or a disproportionate mixture of enantiomers of a pharmacologically active compound, with or without a flux enhancer for percutaneous absorption.

A novel method of administering pharmacologically active chiral compounds using the above mentioned compositions is also disclosed.

DETAILED DESCRIPTION OF THE INVENTION

The applicants have discovered that compositions containing a disproportionate mixture of certain pharmacologically active enantiomers of chiral compounds may be administered transdermally and the flux when applied to the skin will be higher than the flux obtained by transdermal administration of the racemic modification.

The pharmacologically active compounds within the scope of the invention are those for which the racemic modification is solid at or above skin temperature (about $32°-37°$ C.) and wherein the racemic modification has a higher melting point than that of the pure enantiomer or of some enantiomeric mixture containing a disproportionate amount of enantiomers. The solid enantiomeric mixture must belong to the racemic compound class.

Generally, the racemic modification should have a melting point that is at least $5°-10°$ C. higher than the melting point of the enantiomers or of some enantiomeric mixture containing a disproportionate amount of enantiomers. The melting point may be determined according to Wilen et al., *Enantiomers Racemates and Resolutions*, John Wiley & Sons, New York (1981) which is incorporated by reference.

In certain cases it may be advantageous to select a enantiomeric mixture containing a disproportionate amount of enantiomers that exhibit a eutectic melting point. This is advantageous because the lowest melting composition will exhibit the greatest transdermal flux in terms of the total amount of both enantiomers per unit area of skin per unit time. If one isomer has greater pharmacological activity than the other, it may be advantageous to select the disproportionate mixture which yields the highest flux of the more active isomer.

Suitable compounds that may be utilized in the practice of the invention include ephedrine, 3-hydroxy-N-methyl morphinan, propoxyphene, 1,4-dihydropyridine chiral compounds and in particular compounds of the formula:

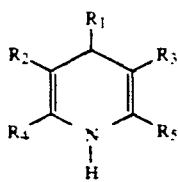

in the form of a pharmacologically active enantiomer wherein $R_1$ is aryl which may have one or more suitable substituents(s) or a heterocyclic group, $R_2$ and $R_3$ are each, same or different, esterified carboxy, and $R_4$ and $R_5$ are each hydrogen, cyano, lower alkyl, or substituted lower alkyl in which the substituent is cyano, hydroxy, acyloxy, hydroxyimino, hydrazino, lower alkoxyimino, hydroxy(lower)alkylimino, N' -or N',N'-di(lower)alkylamino (lower)alkylimino, hydrazino, hydroxy(lower)alkylamino, N'- or N',N'-di(lower)alkylamino(lower)alkylamino, a 5 or 6-membered saturated N-containing heterocyclic-lyl which may have hydroxy, lower alkyl or hydroxy(lower)alkyl, or oxo wherein the thus formed carbonyl may be protected with suitable protecting group; provided that, when one of $R_4$ and $R_5$ is hydrogen or lower alkyl, the other is always cyano or said substituted lower alkyl, and when $R_4$ and $R_5$ are not hydrogen or lower alkyl, both of them are a group selected from cyano and said substituted lower alkyl, or $R_4$ is hydrogen or lower alkyl and $R_3$ and $R_5$ are combined to form a group of the formula:

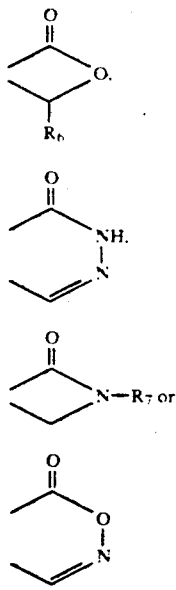

wherein $R_6$ is hydrogen or methyl and $R_7$ is 2-(N,N-diethylamino)ethyl or 2-hydroxyethyl.

The terms used in the definitions of the symbols of the general formulae given in this specification and claims are explained as follows:

The term "lower" used in connection with an alkylene, alkyl and alkenyl is intended to mean the one having 1 or 2 to 8 carbon atoms.

The aryl and aryl moieties may be phenyl, naphthyl, xylyl, tolyl, mesityl, cumenyl and the like, which may have one or more suitable substituent(s). Preferred examples of the suitable substituent(s) are halogen, nitro, hydroxy, halo(lower)-alkyl, lower alkoxy, lower alkenyloxy, cyano, lower alkoxycarbonyl or lower alkylsulfamoyl. The halogen or halo moieties are fluorine, chlorine, bromine or iodine.

Lower alkylene moieties may have a straight or branched and saturated bivalent hydrocarbon chain such as methylene, ethylene, methylmethylene, trimethylene, propylene or tetramethylene.

Lower alkyl and lower alkyl moieties may have a straight or branched and saturated hydrocarbon chain such as methyl, ethyl, propyl, isopropyl, butyl, isobutyl, t-butyl, pentyl, neo-pentyl, hexyl, heptyl or octyl.

Lower alkoxy and lower alkoxy moieties may be methoxy, ethoxy, propoxy, isopropoxy, butyoxy, t-butoxy and pentyloxy.

Halo(lower)alkyl moieties may be mono-halo(lower)alkyl such as chloromethyl, bromomethyl or chloropropyl; di-halo(lower alkyl such as 1,2-dichloroethyl, 1,2-dibromoethyl or 2,2-dichloroethyl; and tri-halo(lower)alkyl such as trifluoromethyl or 1,2,2,-trichloroethyl.

Lower alkenyl and lower alkenyl moieties may be ones having a straight or branched hydrocarbon chain which contains one or more double bond(s), such as vinyl, allyl, butenyl, butanedienyl or penta-2,4-dienyl.

Acyl and acyl moieties may be lower alkanoyl such as formyl, acetyl, propionyl, butyryl, isobutyryl, valeryl, isovaleryl, pivaloyl; substituted lower alkanoyl, for example, carboxy(lower)-alkanoyl, esterified carboxy(lower)alkanoyl such as lower alkoxycarbonyl(lower)alkanoyl, Nor N,N-di-substituted amino(lower)alkanoyl such as Nor N,N-di-(lower)alkylamino(lower)alkanoyl (e.g. N-methyl-(or N,N-diethyl) aminoacetyl, 1(or2)-[N-ethyl(or N,N-diethyl)amino]-proprionyl or 1 (or 2)-[N-methyl-N-ethylamino]propionyl) or N-lower alkyl-N-ar(lower)alkylamino(lower)alkanoyl (e.g. 1-(or 2)-[N-methyl-N-benzylamino]propionyl) or aryloxy(lower)alkanoyl such as phenoxyacetyl, tolyloxyacetyl, 2(or 3 or 4)-chlorophenoxyacetyl, 2-[2(or 3 or 4)-chlorophenoxy]propionyl, 2(or 3 or 4)-nitrophenoxyacetyl or 2(or 3 or 4) methoxyphenoxyacetyl); aroyl such as benzoyl, naphthoyl or toluoyl and the like.

Lower alkoxycarbonyl moieties may be methoxycarbonyl, ethoxycarbonyl, propoxycarbonyl, isopropoxycarbonyl, butoxycarbonyl, t-butoxycarbonyl and the like.

Lower alkylsulfamoyl moieties may be methylsulfamoyl, ethylsulfamoyl, propylsulfamoyl, isopropylsulfamoyl, butylsulfamoyl, pentylsulfamoyl and the like.

A heterocyclic group designated $R_1$ may be an aromatic heterocyclic group containing one or more hetero atom(s) selected form a nitrogen atom, a sulfur atom and an oxygen atom, for example, thienyl, furyl, pyrrolyl, thiazolyl, thiadiazolyl, tetrazolyl, pyridyl, pyrimidinyl, quinolyl, isoquinolyl, benzothienyl, indolyl or purinyl.

Esterifed carboxy groups designated $R_2$ and $R_3$ may be lower alkoxycarbonyl such as methoxycarbonyl, ethoxycarbonyl, propoxycarbonyl, butoxycarbonyl, t-butoxycarbonyl; halo(lower)alkoxycarbonyl such as the haloanalogues of the above-mentioned lower alkoxycarbonyl (e.g., 2-bromoethoxycarbonyl, 2-chloroethoxycarbonyl, 2(or 3)-chloropropoxycarbonyl, 2 (or 3)-bromopropoxycarbonyl, 2,2-dichloroethoxycarbonyl or 2,2,2-trichroloethoxycarbonyl); hydroxy(lower- )alkoxycarbonyl such as 2-hydroxyethoxycarbonyl or 2(or 3)-hydroxypropoxycarbonyl; lower alkoxy(lower)alkoxycarbonyl such as 2-methoxyethoxycarbonyl, 2-ethoxyethoxycarbonyl or 2(or 3)-methoxy(or ethoxy)-propoxycarbonyl; aryloxycarbonyl such as phenoxycarbonyl, tolyloxycarbonyl, xylyloxycarbonyl or p-chlorophenoxycarbonyl; ar(lower)alkoxycarbonyl such as benzyloxycarbonyl, p-bromobenzyloxycarbonyl, O-methoxybenzyloxycarbonyl or phenethyloxycarbonyl; ar(lower)alkoxy (lower)alkoxycarbonyl such as 2-(benzyloxyl)ethoxycarbonyl or 2(or 3)-(benzyloxy)-propoxycarbonyl; aryloxy(lower)alkoxycarbonyl such as 2-(phenoxy)ethoxycarbonyl or 2(or 3)-(phenoxy)-propoxycarbonyl; Nor N,N-(di)-substituted amino(-lower)-alkoxycarbonyl such as Nor N,N-(di)-(lower)-alkylamino(lower) alkoxycarbonyl (e.g., 1(or 2)-[N-methyl(or N,N-dimethyl) amino]ethoxycarbonyl, 1(or2)-[N-ethyl(or N,N-diethyl)amino]ethoxycarbonyl, or 1(or 2)-N-methyl-N-ethylamino)ethoxycarbonyl or lower alkyl-N-ar(lower)alkylamino(lower)alkoxycarbonyl (e.g. 2-(N-methyl-N-benzylamino)ethoxycarbonyl) and the like, and further $R_2$ and $R_3$ may be same or different.

Lower alkyl substituted with oxo includes lower alkanoyl such as formyl, acetyl, propionyl, butyryl, isobutyryl, valeryl, isovaleryl or pivaloyl and lower alkanoyl (lower)alkyl such as formylmethyl, acetonyl, 2-formylethyl, 3-formylpropyl or butyrylmethyl. The carbonyl group thereof may be protected with suitable protecting group, and thus protected carbonyl group in this invention means a group given by protecting the carbonyl with conventionally employed protecting group for a carbonyl. Suitable examples of such protected carbonyl groups are acetal, cyclic-acetal, thioacetal, cyclic-thioacetal, cyclicmonothioacetal or acylal types of group. Examples of these lower alkyl groups containing such protected carbonyl group are gem-di-(lower)alkoxy(lower)alkyl (e.g. dimethoxymethyl, 1,1-dimethoxyethyl, diethoxymethyl, dipropoxymethyl, 2,2-diethoxyethyl or 2,2-diethoxypropyl); gem-lower alkylenedioxy(lower)alkyl (e.g. 1,3-dioxolan-2-yl, 2-methyl-1,3-dioxolan-2-yl, 4-methyl-1,3-dioxolan-2-yl, 4,5-dimethyl-1,3-dioxolan-2-yl, 1,3-dioxan-2-yl, 2-methyl-1,3-dioxan-2-yl, 1,3-dioxolan-2-yl-methyl, 2-methyl-1,3-dioxolan-2-yl-methyl or 3-(1,3-dioxolan-2-yl)propyl); gem-di-(lower)alkylthio(lower)-alkyl (e.g., dimethylthiomethyl, 1,1-dimethylthioethyl, diethylthiomethyl or 2,2-diethylthioethyl); gem-lower alkylenedithio(lower)alkyl (e.g. 1,3-dithiolan-2-yl, 2-methyl-1,3-dithiolan-2-yl, 4-methyl-1,3-dithiolan-2-yl, 4,5-dimethyl-1,3-dithiolan-2-yl, 1,3-dithian-2-yl, 2-methyl-1,3-dithian-2-yl, 1,3-dithiolan-2-yl-methyl, 2-methyl-1,3-dithiolan-2-ylmethyl or 3-(1,3-dithiolan-2yl)propyl); and gem-di(lower)alkanoyloxy(lower)alkyl (e.g., diacetoxymethyl, 1,1-diacetoxyethyl, dipropionyloxymethyl or 2,2-dipropionyloxyethyl); 5 or 6-membered saturated 1-oxa-3-thioheterocyclic-1-yl-(lower)alkyl (e.g., 1,3-oxathiolan-2-yl, 2-methyl-1,3-oxathiolan-2-yl, 4-methyl-1,3-oxathiolan-2-yl, 4,5-dimethyl-1,3-oxathiolan-2-yl, 1,3-oxothian-2-yl, 2-methyl-1,3-oxothian-2-yl, 1,3-oxathiolan-2-ylmethyl, 2-methyl-1,3-oxathiolan2-ylmethyl or 3-(1,3-oxathiolan-2-yl)propyl).

A 5 or 6-membered saturated N-containing heterocyclic-1-yl) group may be one which may contain additional one or more hetero atom(s) selected from nitrogen, sulfur and oxygen atoms such as pyrrolidin-1-yl, piperidino, imidazolidin-1-yl, morpholino or thiomorpholino, and it may be optionally substituted with hydroxy, lower alkyl or hydroxy(lower)alkyl such as hydroxymethyl, 2-hydroxyethyl, 2-hydroxypropyl or 3-hydroxypropyl.

The other terms of each lower alkoxyimino, N'- or N',N'-di-(lower)alkylamino(lower)alkylimino, hydroxy(lower) alkylamino, N'- or N',N'-di(lower)alkylamino(lower)alkylamino and hydroxy(lower)alkylamino will be clearly defined by applying optionally the above given exemplifications of the terms to them.

The preferred compound is nilvadipine.

The (+) or (−) enantiomers may be obtained using standard procedures such as chiral chromatography of the racemate or other means.

Suitable vehicles for use in the transdermal administration of compounds of the invention may be selected by those who are skilled in the art. If desired, a flux enhancer may be used to increase the rate of permeation of the drug. The compositions of the invention may be prepared by admixing the flux enhancer with the drug. The concentration of the drug will depend on the particular drug and the particular enhancer. Generally, solutions of up to and including saturated solutions of the drug may be employed. In addition saturated solutions which contain dispersed, undissolved drug may be used. If desired the flux enhancing agent and drug may be placed in a transdermal patch. In addition other ingredients such as gelling agents; e.g. hydroxypropyl cellulose; viscous adhesive agents; polymeric additives, e.g. thickeners; processing agents; stabilizers; preservatives; UV absorbers; antioxidants; viscosity increasing agents and the like may be added. In the case of the above-mentioned 1,4-dihydropyridines, suitable flux enhancers may be selected from the group consisting of esters of $C_{12}$–$C_{18}$ fatty acids with $C_1$–$C_6$ straight and branched chain alcohols; diesters of aliphatic diacids of the formula:

$R_8$ OOC $(CH_2)_n$ COO $R_9$ wherein n is a whole integer from 2–8; $R_8$ and $R_9$ may be the same or different and are selected from the group consisting of $C_2$ to $C_{12}$ straight and branched chain alcohols; and compounds of the formula:

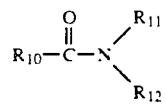

wherein $R_{10}$ is a $C_7$–$C_{13}$ straight or branched chain alkyl or alkenyl group $R_{11}$ and $R_{12}$ are the same or different and are selected from —CH and —CH$_2$CHOHCH$_3$ and hydrogen; benzyl alcohol, 2-phenylethanol, ethanol or mixtures thereof with ethyl alcohol.

The $C_{12}$–$C_{18}$ fatty acids include lauric, tridecanoic, myristic, pentadecanoic, palmitic, margaric, stearic and the like. The straight and branched chain alcohols include methanol, ethanol, n-propanol, isopropanol, n-pentanol; n-hexanol and the like.

The diesters include the diesters of succinic, glutaric, adipic, pimelic, suberic, azelaic and sebacic acids with ethanol, n-propanol, isopropanol, n-hexanol, n-octanol and the like.

Compounds of the formula:

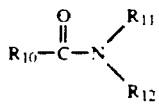

include those where $R_{10}$ is capryl, undecanyl, lauryl 3-octenyl, 4-decenyl, 9-decenyl or tridecanyl and $R_{11}$ and $R_{12}$ are ethylhydroxy or propylhydroxy. The compound N,N-diethylhydroxylauramide is preferred.

Ethanol may be employed at levels that are sufficient to modify the flux. It may comprise from 10-95% of the total flux enhancer. Light mineral oil or silicones may be employed to control the thermodynamic activity of the flux enhancers. Useful silicones include polydimethylsiloxanes. The amount of such materials may be varied to change the rate of absorption of a drug from a particular flux enhancer.

Illustratively, compositions can be provided and used which comprise nilvadipine, 0.01 to 50% by weight with the balance comprising either the flux enhancer alone or flux enhancer in combination with other additives.

DESCRIPTION OF THE PREFERRED EMBODIMENT

The following example illustrates the present invention. It is not to be construed to limit the claims in any manner whatsoever.

EXAMPLE 1

By way of illustration the following table shows the solubility in mg/ml at 32° C. of the racemic modification and the (+) enantiomer of nilvadipine in different solvents.

TABLE I

|  | Polyethylene glycol 400 (30% w/w in $H_2O$) | Ethanol | Diisopropyl Adipate |
|---|---|---|---|
| nilvadipine (±) | 0.08 | 38 | 56 |
| nilvadipine (+) | 0.115 | 170 | 142 |

The transdermal penetration rate of the racemic modification and the (+) enantiomer of nilvadipine was determined by determining the permeation rate through split-thickness human cadaver skin.

After removal from a donor, the cadaver skin is placed in a nutrient medium (Dulbecco's Minimum Essential Medium containing a mycostat and a bacteriostat) on a collagen pad. A disc of skin about 2 cm in diameter is cut and placed in a Bronaugh transdermal transport cell at 32° C. The dermal surface is contacted with a receptor fluid that consists of polyethylene glycol 400 as a 30% w/w solution in water. A saturated solution of the drug is placed on the skin with a dropper and the flux value is read after steady state conditions have been reached. Carbon-14 labeled drug and a calibrated scintillation counter is used to determine the amount of drug transported.

The permeation rate through split-thickness human cadaver skin of the solution set forth in Table I are reported in Table II in terms of nanograms/cm²/hour.

TABLE II

| Vehicle | Racemic Modification | Enantiomer |
|---|---|---|
| 30% w/w PEG 400 in water | 5 | 28 |
| Diisopropyl | 360 | 850 |

TABLE II-continued

| Vehicle | Racemic Modification | Enantiomer |
|---|---|---|
| Adipate |  |  |
| Ethanol | 150 | 560 |

The results set forth in Table II show that solutions of the enantiomer of nilvadipine are more rapidly absorbed than solutions of the racemic modification.

The enantiomer or mixtures of enantiomers of the invention may be placed in a transdermal delivery system for administration.

EXAMPLE 2

Saturated aqueous solutions of ephedrine racemic compound and ephedrine (1R,1S) enantiomer were prepared and placed in separate Bronaugh flow through permeation cell using normal saline as the receptor fluid and a temperature of 32° C. Cryopreserved human cadaver skin from the same donor was used for both solutions. The concentration of ephedrine in the receptor solution was determined by ultraviolet absorbance spectrophotometry. The results were as follows:

| Material | Mean Flux (0-24 hrs.) (mg/cm²/hr) |
|---|---|
| Ephedrine Racemic | 0.52 |
| (1R, 2S) Ephedine Enantiomer | 2.40 |

The results of this example show that the enantiomer of ephedine has almost a nine fold greater flux than the racemate.

We claim:

1. A pharmaceutical composition for transdermal administration which comprises:
   (a) an amount of a substantially pure enantiomer or an enantiomer mixture containing disproportionate amounts of enantiomers of a pharmacologically active chiral compound wherein the racemic modification of said pharmacologically active compound has a melting point that is 5° C. or more above the melting point of the pure enantiomer or of said enantiomer mixture; and
   (b) a vehicle for said pharmacologically active chiral compound.

2. A pharmaceutical composition as defined in claim 1 wherein the substantially pure enantiomer is employed.

3. A pharmaceutical composition as defined in claim 1 wherein an enantiomer mixture is employed that contains disproportionate amounts of enantiomers that form a eutectic.

4. A method for the administration of a pharmaceutical composition which comprises:
   (a) an amount of a substantially pure enantiomer or an enantiomer mixture containing disproportionate amounts of enantiomers of a pharmacologically active chiral compound wherein the racemic modification of said pharmacologically active compound has a melting point that is 5° C. or more above the melting point of the pure enantiomer or of said enantiomer mixture; and
   (b) a vehicle for said pharmacologically active chiral compound, said method comprising contacting the skin of a host in need of treatment with said compositions.

5. A method as defined in claim 4 wherein the substantially pure enantiomer is employed.

6. A method as defined in claim 4 wherein an enantiomer mixture is employed that contains disporportionate amounts of enantiomers that form a eutectic.

* * * * *